United States Patent [19]

Schulman

[11] 4,411,651
[45] Oct. 25, 1983

[54] DEVICE AND METHOD USEFUL IN MONITORING FLUID FLOW IN A DRUG INJECTOR

[75] Inventor: Joseph H. Schulman, Los Angeles, Calif.

[73] Assignee: Pacesetter Systems, Inc., Sylmar, Calif.

[21] Appl. No.: 266,835

[22] Filed: May 26, 1981

[51] Int. Cl.³ ............................................. A61M 5/00
[52] U.S. Cl. .................................... 604/151; 604/891; 604/67; 604/246; 417/63; 73/861.08
[58] Field of Search ................... 128/260, 273, 214 E, 128/214 F, 213 R; 73/861, 861.01, 861.02, 248; 604/891, 30-34, 65-67, 246, 250, 249, 151; 417/63

[56] References Cited

U.S. PATENT DOCUMENTS 4,137,913  2/1979  Georgi ........................ 128/214 F
4,207,871  6/1980  Jenkins ...................... 128/214 F X
4,303,376  12/1981  Siekmann ................... 128/214 F

OTHER PUBLICATIONS

Spencer et al, IEEE Transactions of Sonic and Ultrasonics, vol. su-25, No. 3 (May, 1978).

Primary Examiner—Kyle L. Howell
Assistant Examiner—John C. Hanley
Attorney, Agent, or Firm—John F. Buskirk

[57] ABSTRACT

A fluid flow monitoring method and device for a drug injector (10). More particularly, a flow monitoring device is disclosed for an implantable or externally located drug injector having a conduit (18) for carrying fluid from a reservoir (14) to a user's body. In an exemplary embodiment, the drug injector (10) is of the type having a first valve (22) located proximal to the reservoir (14) for blocking the flow of fluid through the conduit (18), a second valve (24) located distal to the reservoir (14) for blocking the flow of fluid through the conduit (18), and a pump (20) located between the first and second valves (22) and (24) for alternately increasing and decreasing the volume of a conduit portion (68) located between the first and second valves (22) and (24). The valves are controlled so that the first valve (22) is open and the second valve (24) closed when the pump (20) is increasing the volume of its associated conduit portion, thereby drawing fluid from the reservoir (14) into the conduit (18). The valves are further controlled so that the first valve (22) is closed and the second valve (24) open when the pump (20) is decreasing the volume of its associated conduit thereby forcing fluid from the conduit (18) into the user's body. The fluid flow monitoring device includes circuitry for generating signals related to the electrical resistance of the fluid across the first and second valves (22) and (24), and the conduit portion (68) whose volume is affected by the pump (20). These signals are utilized to continually determine the configuration of each valve and the volume of the conduit portion (68). This information can be utilized to calculate fluid flow through the conduit (18).

24 Claims, 6 Drawing Figures

DEVICE AND METHOD USEFUL IN MONITORING FLUID FLOW IN A DRUG INJECTOR

TECHNICAL FIELD

The invention relates to a drug injector, and more particularly to a device useful in monitoring fluid flow from the injector to a user.

BACKGROUND ART

Drug injectors such as insulin injectors have recently been developed for users having a need for periodic and continual drug injections. These drug injectors can be either implanted or externally located with respect to the user's body. A typical user of a drug dispensing injector or device would be a diabetic having a requirement for insulin injections whose amounts are related to the time, quantity, and type of food intake. Proper amounts of insulin for such a user are essential for health and even life itself, and it is therefore essential for the user to know the amount of insulin being dispensed as well as the amount of insulin remaining in a reservoir, especially in the case of an implanted device. One method of determining the amount of fluid remaining in the reservoir is to note each drug injection time and the amount of drug to be dispensed. A running total of the amount of drug dispensed since the last reservoir refill can then be maintained. Such a method would be somewhat satisfactory if the dispensing apparatus always functioned as intended; however should it dispense slightly more fluid than intended due to a malfunction of some type, then the reservoir could run out of fluid at an unexpected and inconvenient time. A more positive method of determining the amount of fluid remaining within the reservoir would be to actually measure flow rate from the reservoir each time that the drug is dispensed. This flow rate and the time during which the flow rate existed would provide a precise indication of the amount of fluid removed from the reservoir. The present invention provides a means useful for determining the flow rate which in turn can be utilized to calculate the amount of fluid remaining in the reservoir.

STATEMENT OF THE INVENTION

In a fluid dispensing device having a conduit for carrying fluid from a reservoir means to a user's body, a first valve means located proximal to the reservoir means for restricting the flow of fluid through the conduit, a second valve means located distal to the reservoir means for restricting the flow of fluid through the conduit, and a pump means located between the first and second valve means for alternately increasing and decreasing the volume of a portion of the conduit between the first and second valve means, the invention provides a means useful for measuring fluid flow including a first means for generating a first signal related to the electrical resistance of the fluid within a first predetermined portion of the conduit, the first predetermined portion containing the first valve means; a second means for generating a second signal related to the electrical resistance of the fluid within a second predetermined portion of the conduit whose volume is alternately increased and decreased; and a third means for generating a third signal related to the electrical resistance of the fluid portion within a third predetermined portion of the conduit, the third predetermined portion containing the second valve means, whereby the first, second, and third signals can be utilized to calculate the flow rate of the fluid through the conduit. In addition, the invention provides a method useful for measuring fluid flow through the conduit.

In one exemplary embodiment utilizing an implantable drug injector, first electrode pairs are located across the first valve means, pump means, and second valve means, each electrode pair being connected to a separate current source. Second electrode pairs are provided, one of which is located between each of the first electrode pairs and across their respective first valve means, pump means and second valve means. Each of the second electrode pairs is utilized to measure the voltage drop of the fluid therebetween, this voltage drop being related to the electrical resistance provided by the fluid. Signals related to these voltage drops are telemetered to an external receiving means. The invention utilizes the principle that electrical resistance is directly related to the cross-sectional area of the channel defined by the conduit and its associated valve means or pump means. Thus, signals directly related to the electrical resistance across the first and second valve means and the pump means can be utilized to define their configurations as they alter cross-sectional areas of the conduit. When the configuration of the pump means and valve means are known, flow rate through the conduit can be readily determined. In accordance with a further feature of the invention, a means for directly measuring the resistivity of the fluid is provided by utilizing the relationship $R=\rho(L/A)$ where $R$=resistance, $\rho$=resistivity, $L$=length, and $A$=the cross-sectional area through which the fluid flows. Resistivity is calculated by measuring the resistance of fluid contained in a conduit portion having a constant cross-sectional area. Although the exemplary embodiment provides for each of the resistance related signals to be telemetered to an external receiving means, the resistance-related signals could be provided to an implanted computational unit for a direct calculation of fluid flow and the fluid remaining in the reservoir, the results of this calculation being telemetered to an external receiving means in response to an externally generated interrogation signal.

DETAILED DESCRIPTION

Detailed illustrative embodiments of the invention disclosed herein exemplify the invention and are currently considered to be the best embodiments for such purposes. They are provided by way of illustration and not limitation of the invention. Various modifications thereof will occur to those skilled in the art, and such modifications are within the scope of the claims which define the present invention.

As previously explained, a device useful for the measurement of fluid flow is disclosed for a fluid dispensing device having a conduit for carrying fluid from a reservoir contained therein to a user's body. Positioned along the conduit is a first valve which is located proximal to the reservoir for blocking the flow of fluid through the conduit, a second valve located distal to the reservoir for blocking the flow of fluid through the conduit, and a pump located between the first and second valves which alternately increases and decreases the volume of a conduit portion between the first and second valves. Such a pump is commonly known as a peristaltic pump. By proper cycling of the valves, the pump can be utilized to push fluid through the conduit when the second valve is open and the first valve is closed, and then to draw fluid from the reservoir when the first valve is open and the second valve is closed. The device disclosed continuously generates signals related to the electrical resistance of the fluid across the first valve, across the conduit portion whose volume is altered by the pump, and across the second valve. The position of each valve and the pump can be accurately determined from these signals, thereby providing information necessary to calculate the flow rate through the conduit.

Figure 1:
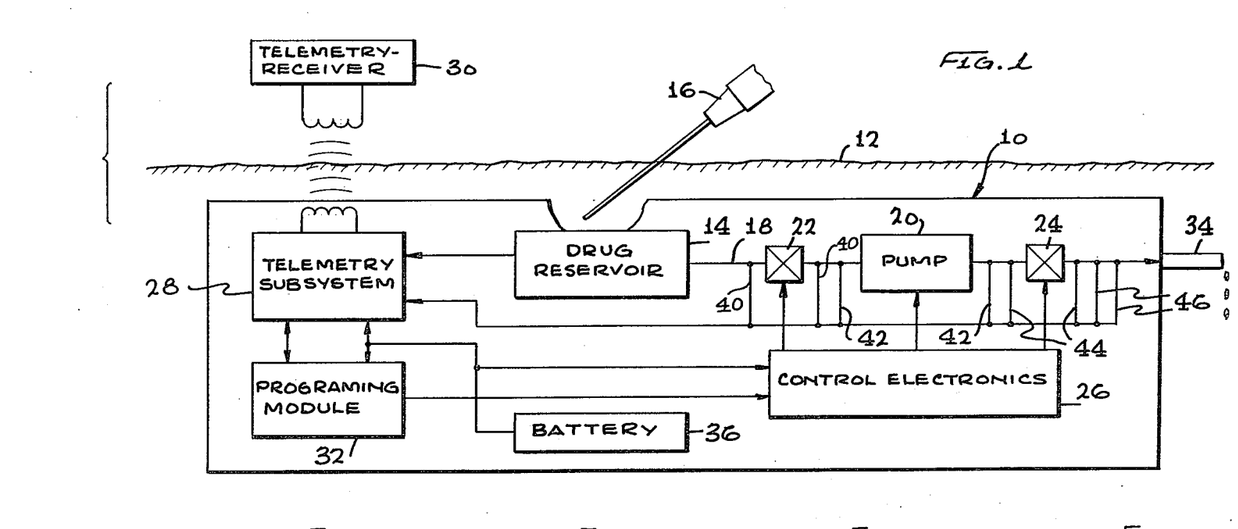
FIG. 1 is a block diagram of an implantable fluid dispensing device incorporating a fluid flow monitoring means provided by the invention.

Referring to FIG. 1, an implantable drug injector 10, which could be an insulin dispenser for a diabetic, is shown implanted beneath the skin 12 of a user. Although an implanted drug injector is utilized for illustrative purposes, the injector could also be externally located with respect to the user's body. A drug reservoir 14 is located so that it can receive a fluid drug to be dispensed via an externally controlled hypodermic 16. A conduit 18 provides fluid communication between the drug reservoir 14 and the user's body. A pump 20 and associated piston 66 is in pressure communication with the conduit 18 and alternately increases and decreases the volume of a portion of the conduit 18. A first valve 22 and a second valve 24 are located in series with the conduit 18, positioned on each side of the pump 20, and controlled in synchronism with the pump 20, thereby defining a peristaltic pump. This synchronized operation is effected by a control electronics unit 26 so that when the pump 20 is drawing fluid from the reservoir 14 by increasing the volume of the conduit portion, the first valve 22 will by open and the second valve 24 will be closed, and when the pump is forcing fluid through the conduit to the user's body by decreasing the volume of the conduit portion, the first valve 22 will be closed and the second valve 24 will be open. As will be explained in detail below, voltages related to the resistance of the fluid across the first valve 22, the pump 20 and the second valve 24 are continuously generated, and provided to a telemetry subsystem 28 from which they are transmitted to an externally located telemetry receiver 30. A programming module 32 is in communication with the telemetry subsystem 28 and the control electronics unit 26 for controlling the pump 20, the first valve 22 and the second valve 24 in accordance with a desired dispensing rate for the fluid. The fluid is dispensed into the body through a dispensing aperture 34. Power is supplied to the telemetry subsystem 28, programming module 32, and control electronics unit 26 by a battery 36. Although a solenoid-type pump 20 is shown in the exemplary embodiment, it should be understood that other types of pumps could be utilized, one example being a piezoelectric pump.

In operation, the drug reservoir 14 is filled with the appropriate fluid by the hypodermic 16. As previously explained, the pump 20 is of the type which alternately reduces and increases the volume of a portion of the conduit 18. When the volume of the conduit portion is being increased, the control electronics unit 26 generates the appropriate signals to close the second valve 24 and open the first valve 22. An increase in conduit volume caused by the pump 20 draws fluid from the reservoir 14 and through the first valve 22 which is open. As the pump 20 begins to reduce the volume of the conduit portion, the control electronics unit 26 provides the appropriate signals for causing the first valve 22 to close and the second valve 24 to open. The decrease in conduit volume then forces the fluid through the second valve 24 and the dispensing aperture 34 to the user's body. As can be appreciated, when the volume of the conduit portion affected by the pump 20 is known, and the status of the first and second valves 22 and 24 are known, flow rate through the conduit 18 can be accurately determined. The monitoring device disclosed provides a means for determining these parameters simply and accurately.

Although two valves 22 and 24 are shown in the exemplary embodiment, the drug injector 10 can also operate utilizing only the first valve 22 or the second valve 24 in conjunction with the pump 20. For example, if only the first valve 22 and the pump 20 are provided, then they are synchronized so that the valve 22 is open when the pump 20 is increasing the volume of a portion of the conduit 18, and the valve is closed when the pump 20 is decreasing the volume of a portion of the conduit 18. Similarly, if only the second valve 24 and the pump 20 are provided, they are synchronized so that the valve 24 is closed when the pump 20 is increasing the volume of a portion of the conduit 18, and the valve 24 is open when the pump 20 is decreasing the volume of a portion of the conduit 18. These two configurations will result in fluid moving from the drug reservoir 14 through the dispensing aperture 34, although at a lower rate than that obtained with the two valve configuration.

As is well understood by those familiar with basic circuit theory, electrical resistance of a substance is equal to the resistivity $\rho$ multiplied by the length L of the conductor and divided by its cross-sectional area A ($R = \rho L/A$). Thus, if the length of the conductor remains constant, and the resistivity remains constant, then the resistance of the conductor is inversely proportional to its cross-sectional area. This principle is utilized by the present invention to determine the flow rate through the conduit 18 by generating signals related to the fluid's resistance across the first valve 22, across the pump 20 and across the second valve 24. Thus, as the first valve 22 closes to block fluid flow through the conduit 18, a signal related to the electrical resistance across the valve 22 is a direct indication of the position of the valve 22 with respect to the conduit 18. As flow is cut off, the cross-sectional area of the conduit decreases, thereby increasing the electrical resistance. In a similar manner, the electrical resistance created by the fluid across the second valve 24 is indicative of its position with respect to the conduit 18. Similarly, volume changes in the conduit portion affected by movement of the pump piston 66 can be determined by generating a signal related to the resistance of the fluid across the portion of the conduit whose cross-section is affected by the position of the piston 66, this resistance being related to the piston 66 position with respect to the conduit. Thus, by determining these volume changes and determining the positions of the first and second valves 22 and 24 with respect to the conduit 18, an accurate determination of fluid flow through the conduit 18 can be made.

Figure 2:
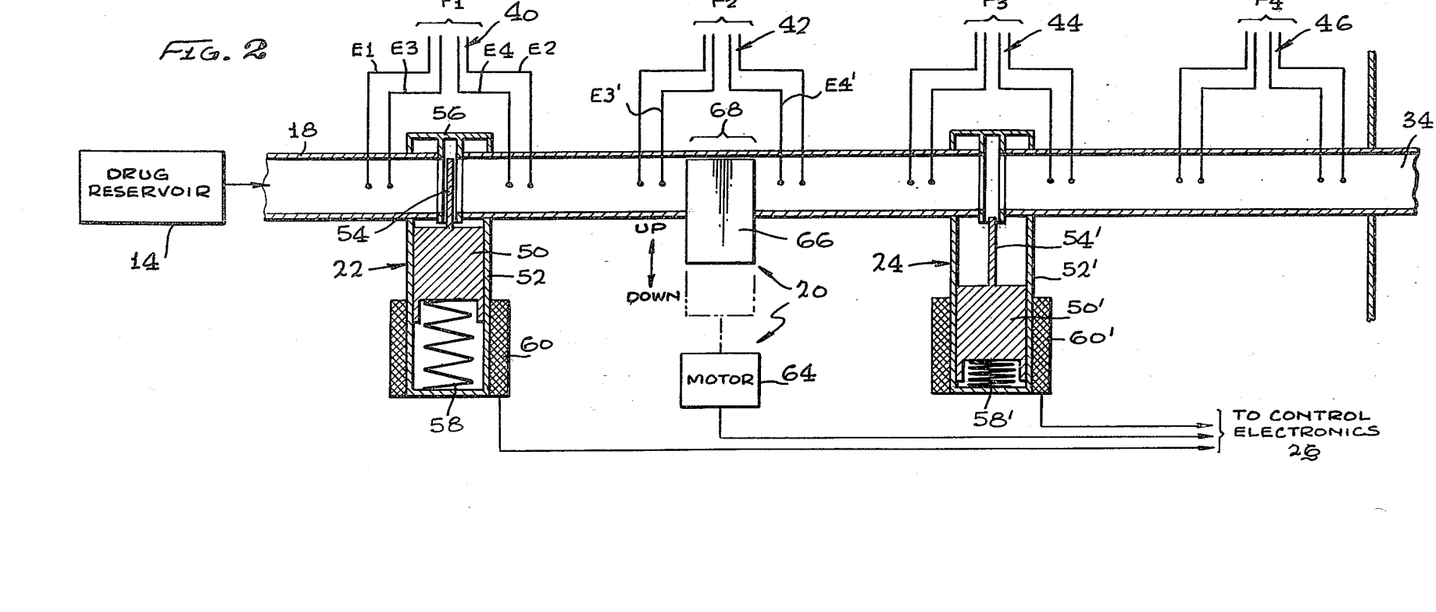
FIG. 2 is a cross-sectional diagram of the fluid dispensing conduit showing the pump, first and second valves and various electrodes.

Referring to FIG. 2, voltage related to the electrical resistance of the fluid across the first valve 22 is developed by a first set of electrodes 40, across conduit portion affected by the pump piston 66 by a second set of electrodes 42, and across the second valve 24 by a third set of electrodes 44. A fourth set of electrodes 46 is provided in a portion of the conduit 18 which has a constant cross-sectional area. Thus, the fourth set of electrodes can be utilized to calculate resistivity $\rho$ because the length over which fluid resistance is determined and the cross-sectional area of the conduit remain constant. This resistivity value can then be utilized for calibrating signals related to resistance from the first, second and third sets of electrodes 40, 42, and 44, respectively. This calibration is important if the fluid tends to experience resistivity changes as it is stored. Referring again to FIG. 2, details of the pump 20, first valve 22, second valve 24 and placement of the electrode sets can be seen. The first valve 22 includes a piston 50 located in a sleeve 52. The piston 50 has a blade 54 connected to its top, the blade 54 being positioned in a holding structure 56 which secures both ends of the conduit 18. The blade 54 and holding structure 56 form a gate in the conduit 18, the gate being closed when the blade 54 is in the position shown for the first valve 22. The blade is held in the closed position by a spring 58. Referring to the second valve 24, the lower portion of the sleeve 52' includes a solenoid switch 60' which, when activated, draws the piston 50' downwardly through the sleeve 52' into the position shown. When in this configuration, fluid can flow through the dispensing aperture 34. Other elements of the second valve 24 are the same as those described for the first valve 22. The solenoids 60 and 60' are operated by the control electronics unit 26 so that the two blades 54 and 54' operate 180 degrees out of phase with respect to each other.

The pump 20 includes the motor 64 and a flow restricting piston 66 which alternately increases and decreases the volume of a conduit portion as designated by the brackets 68. The solid lines show the piston 66 in the up position so that the volume within the portion shown at 68 is at a minimum. At this point, and while the piston 66 is moving from a down position to an up position, the first blade 54 is positioned as shown to block fluid from flowing backwardly into the drug reservoir 14. The second blade 54' is shown fully retracted so that fluid flow will be outwardly through the dispensing aperture 34. However, once the piston 66 begins moving downwardly, the solenoid 60 of the first valve is activated to withdraw the blade 54, and the solenoid 60' of the second valve is deactivated so that the spring 58' will cause the blade 54' to move upwardly and block fluid flow through the conduit 18. As a result of this change in configuration, the additional volume of the conduit portion 18 resulting from the downward movement of the piston 66 will draw fluid from the reservoir 14 into the conduit 18. As can be seen, the first set of electrodes 40 comprises four electrodes E1, E2, E3, and E4 that are placed across the first valve 22 for generating a signal related to the resistance of the fluid between electrodes E3 and E4 as will be explained below. Each of the other sets of electrodes 42, 44 and 46 also comprises four electrodes.

Figure 3:
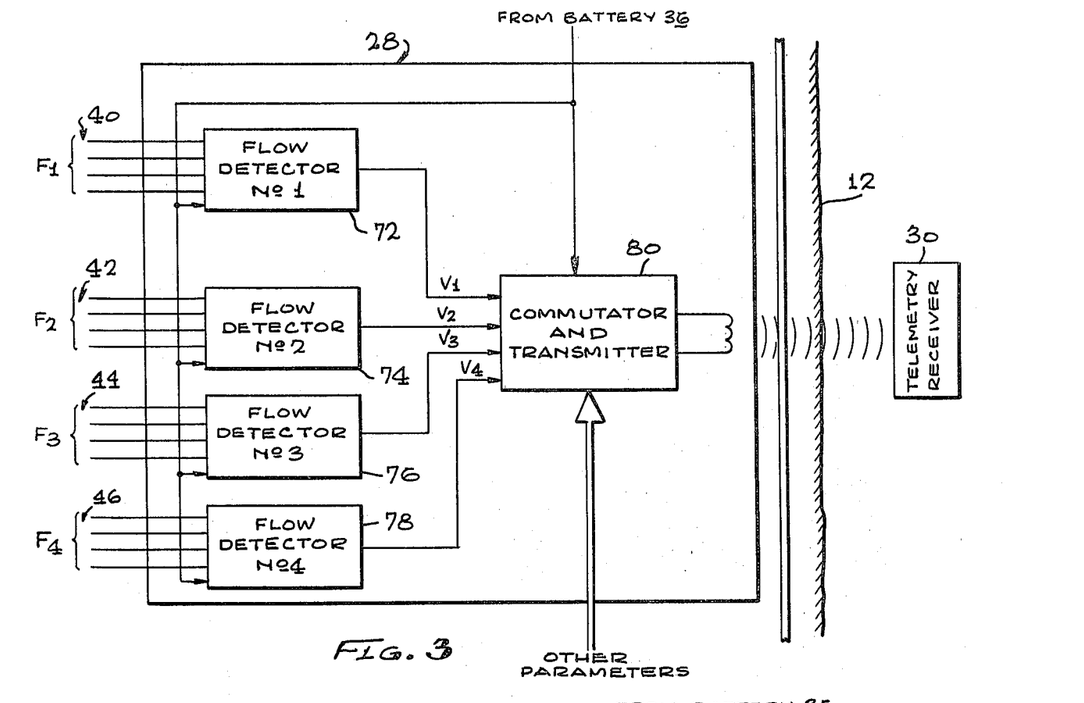
FIG. 3 is a block diagram showing the interface between the various electrodes and the telemetry subsystem.

The telemetry subsystem 28 partially shown in FIG. 3 includes, first, second, third and fourth flow detectors 72, 74, 76 and 78 respectively. The flow detectors, to be described below, provide output voltages V1, V2, V3 and V4 each of which is related to the resistance measured by their corresponding electrode sets 40, 42, 44 and 46. These voltages are provided to a commutator and transmitter 80 which is in communication with the externally located telemetry receiver 30.

Figure 4:
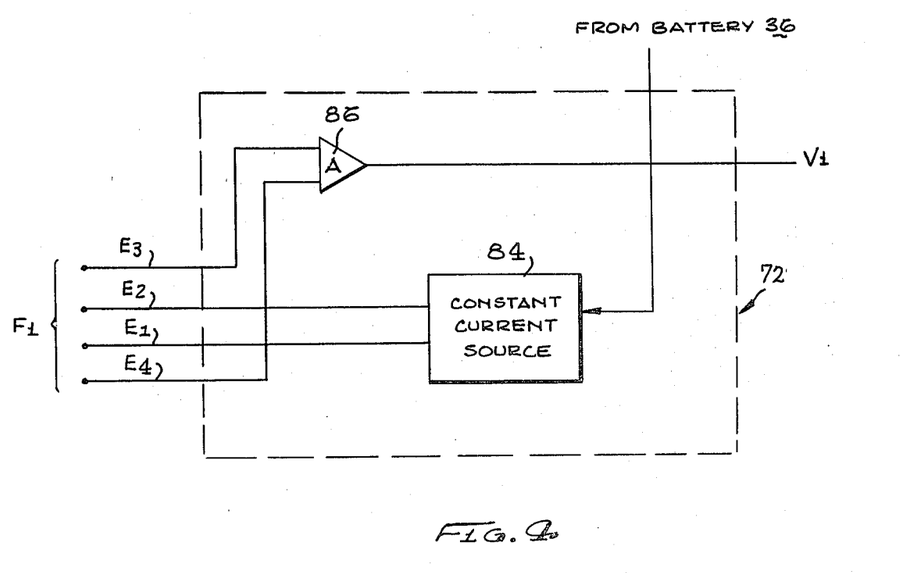
FIG. 4 is a block diagram of one of the flow detectors shown in FIG. 3.

The first flow detector 72 can be seen in FIG. 4, the other three flow detectors 74, 76 and 78 being identical to the first one 72. A constant current source 84 is powered by the battery 36, and is chosen to provide a constant current flow through the first two electrodes E1 and E2 which are located across the first valve 22 as shown in FIG. 2. As the fluid resistance between the first electrode E1 and the second electrode E2 increases, the voltage drop across these two electrodes must also increase to maintain a constant current flow. The third and fourth electrodes, E3 and E4, are positioned across the first valve 22 and within the conduit portion bracketed by the first and second electrodes E1 and E2. The third and fourth electrodes E3 and E4 sense the voltage drop in the fluid between them, this voltage drop being directly related to its resistance as previously explained. The voltage drop is amplified by an amplifier 86. Four electrodes are perferred for the measurement in order to eliminate measurement uncertainties created by voltage drops between each of the current-providing electrodes E1 and E2 and the fluid in the conduit. Thus the third and fourth electrodes E3 and E4 are only used to sense a voltage differential and do not draw current from the fluid.

Figure 5:
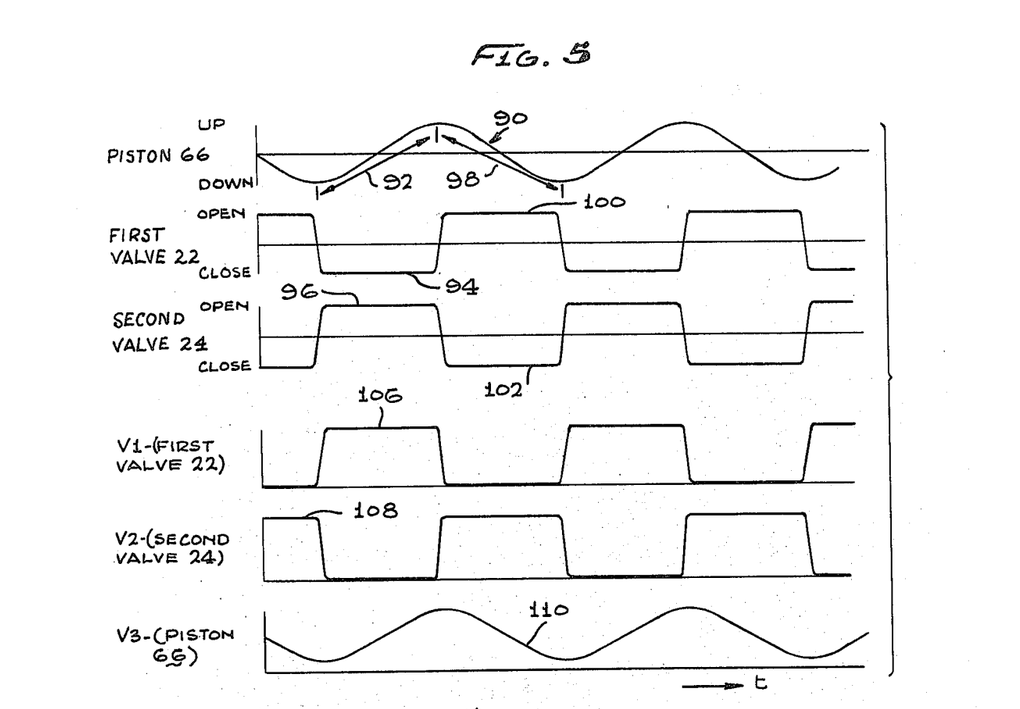
FIG. 5 is a waveform diagram showing the relationship between the first valve, pump, and second valve positions and the voltage drops measured by their corresponding second electrode pairs.

Operation of the fluid flow monitoring device can be visualized in conjunction with the waveforms of FIG. 5 and the diagram of FIG. 2. Referring to FIG. 5, the position of the pump piston 66 with respect to time can be seen in waveform 90. During the period that the piston 66 is moving from a down to an up position as shown at 92, the first valve 22 is fully closed as shown at 94 and the second valve 24 is fully open as shown at 96. Thus, as the piston 66 is moving upwardly and decreasing the volume of the conduit 18, fluid contained in the conduit is forced outwardly through the second valve 24. Similarly, when the piston 66 is moving from an up position to a down position as shown at 98, the first valve 22 is fully open as shown at 100 and the second valve 24 is fully closed as shown at 102. Thus, fluid is drawn from the reservoir through the first valve 22 into the increasing volume created by the piston 66 moving downwardly. The voltage drop sensed by the third and fourth electrodes E3 and E4 across the first valve 22 can be seen in waveform 106 and the voltage drop across the second valve 24 in waveform 108. The voltage across the conduit portion 68 affected by the piston 66 can be seen in waveform 110. The voltage V3 defined by waveform 110 provides a direct indication of position and rate of movement of the piston 66 with respect to the conduit 18. This combined with the configuration of the first and second valves 22 and 24 as shown by V1 and V3, respectively, define the amount of fluid flowing from the reservoir 14 through conduit 18. An externally located receiving means provides this information to a relatively simple calculation device which can precisely calculate flow rate and present that information to the user or his physician. Alternatively, th calculation could be made and the results stored in the fluid dispensing device itself, and an alarm means incorporated to alert the user when reservoir fluid is getting low.

Figure 6:
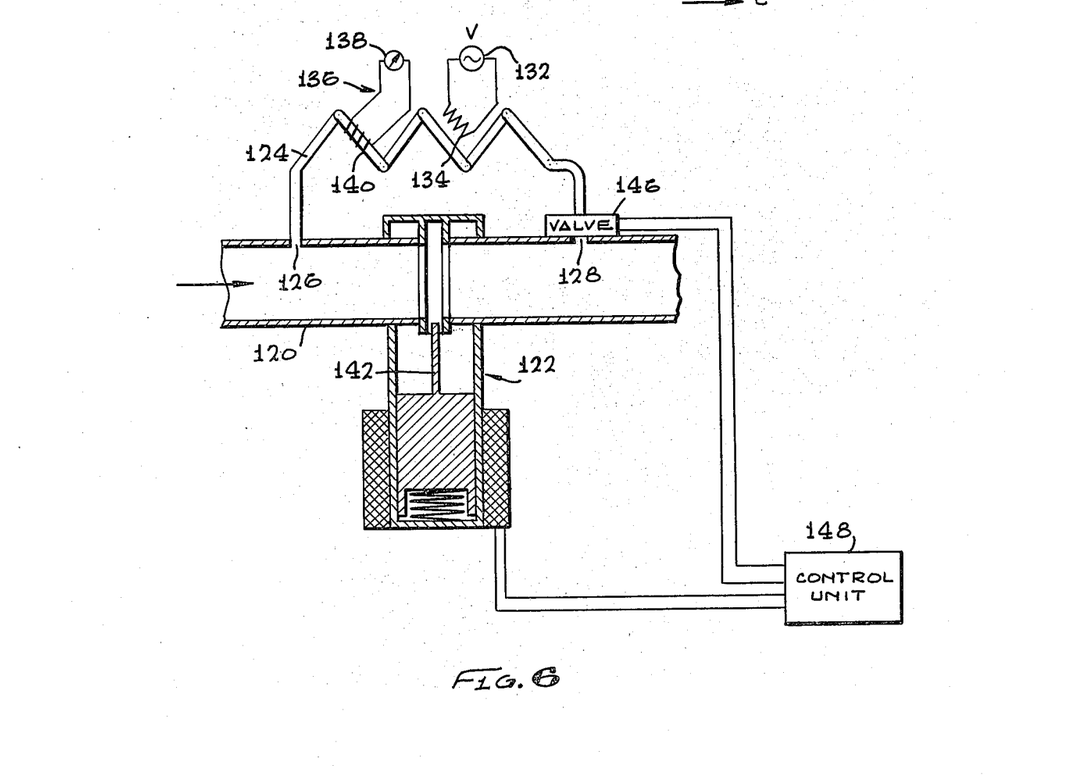
FIG. 6 is a cross-sectional diagram of the fluid dispensing conduit showing the first valve and a further embodiment of a monitoring means for determining the electrical resistance of the fluid.

As can be seen in FIG. 2, the electrodes E1, E2, E3, and E4 directly contact fluid flowing within the conduit 18. It may be desirable or even mandatory that certain types of drugs not come into metallic contact with the electrodes as the drug flows from the reservoir 14 through the aperture 34. For these drugs, another monitoring device for measuring electrical resistance of the fluid across either the valves or the pump is shown in FIG. 6. Referring now to FIG. 6, a conduit 120 having a valve 122 positioned so as to cut off fluid flow trhough the conduit is shown. The valve 122 is identical to the valves 22 and 24 shown in FIG. 2. Although a valve 122[13] is shown in FIG. 6, the monitoring device to be described could also be utilized if the valve 122 were replaced by the pump 20 shown in FIG. 2, or another type of pump such as a piezoelectric pump.

Referring again to FIG. 6, a spirally-configured tube 124 is provided, the tube 124 having a diameter that is small with respect to the diameter of the conduit 120. The tube 124 ends are in fluid communication with the conduit 120 at first and second apertures 126 and 128, respectively. The apertures 126 and 128 are located on opposite sides of the conduit volume through which resistance is to be measured. Thus in the exemplary embodiment shown, the valve 122 is located between the two apertures 126 and 128. An alternating voltage source 132 is connected to an energizing coil 134 which is an electromagnetic coupling relationship to the tube 124 so that energy from the voltage source 132 is coupled to fluid contained within the tube 124. This coupling results in a current flow through the fluid path defined by the tube 124 and the conduit 120 portion between the first and second apertures 126 and 128. Thus, when the valve 122 is in the condiguration shown in FIG. 6, current will flow through the tube 124 and the conduit portion between the two apertures 126 and 128. When the valve 122 is closed as shown in the configuration for the first valve 22 of FIG. 2, then no current will flow through the tube 124 because the valve interrupts a conduction path between the two apertures 126 and 128. A sensing device 136 includes a readout meter 138 and sensing coil 140. The sensing coil 140 is wrapped around the tube 124 and detects any alternating current flowing therethrough. This detected current can then be read on the readout meter 138 or provided to any other suitable monitoring device (not shown). As explained in conjunction with FIG. 2, the current flowing through the conduit 120 is directly related to the cross-sectional area of the conduit 120, this cross-sectional area being a function of the position of the blade 142 with respect to the conduit. When the blade 142 is in the configuration shown in FIG. 6, current will be at a maximum; when the blade is in the configuration shown for valve 22 in FIG. 2, current will be at a minimum. Thus monitoring of the readout meter 138 provides a signal that is related to the cross-sectional area of the conduit 120 amd the position of the blade 142 with respect to the conduit 120.

In order to prevent fluid coupling between each side of the valve 122, an auxilliary valve 146 is provided, the valve 146 configuration with respect to the tube 124 being synchronized with movement of the blade 142 by a control unit 148 so that when the blade 142 is in a blocking position with respect to the conduit 120, the valve 146 will also block fluid flow through the tube 124.

It should also be apparent that the monitoring means of FIG. 6 could be placed across the pump 20 as it alternately increases and decreases the volume of the conduit 120, the current through the tube 124 being directly proportional to the position of the pump 20 with respect to the conduit 120. If the diameter of the tube 124 is sufficiently small with respect to the diameter of the conduit 120, then it would be possible to eliminate the valve 146 as long as some fluid flow through the tube 124 is acceptable as the pump 20 alternately increases and decreases the conduit 120 volume.

What is claimed is:

1. In a peristaltic pump having a conduit and at least one valve means for restricting fluid flow through said conduit, a means for determining the position of said valve means comprising monitoring means for generating a signal related to the electrical resistance of fluid between two points located within said conduit and on opposite sides of said valve means, said electrical resistance being related to the cross-sectional area of a portion of said conduit whose cross-sectional area is altered by said valve means, said electrical resistance thus being related to the position of said valve means.

2. The means for determining of claim 1 wherein said peristaltic pump is an implantable pump.

3. The means for determining of claim 1 wherein said monitoring means comprises:
   a pair of electrodes each located at one of said two points; and
   a flow detector for generating a first voltage related to the electrical resistance between said pair of electrodes.

4. The means for determining of claim 1 wherein said monitoring means comprises:
   a constant current source;
   a first pair of electrodes each located so as to bracket said two points located within said conduit current source;
   a second pair of electrodes located within said conduit at said two points; and
   means for measuring the voltage drop between said second pair of electrodes, said voltage drop comprising said signal.

5. The means for determining of claim 1 wherein said monitoring means comprises:
   a tube having both ends in fluid communication with said conduit, the two ends being on opposite sides of said valve means;
   means for inducing a voltage differential across the fluid present in both ends of said tube; and
   means for measuring current flow through said tube, said current flow being related to the cross-sectional area of said conduit portion located between said tube ends.

6. In a device for dispensing fluid into a user's body, a means useful for measuring fluid flow through a fluid-dispensing conduit of said device comprising:

first means for generating a signal related to the electrical resistance of fluid within a portion of said conduit; and second means responsive to said first means for telemetering a signal related to the resistance of said fluid to a telemetry receiving device, whereby the electrical resistance of said fluid within said conduit portion is related to the cross-sectional area of said conduit portion and said cross-sectional area is related to fluid flow through said conduit.

7. In a device for dispensing fluid into a user's body, said device including a conduit in fluid communication with a fluid-containing reservoir, a means useful for measuring fluid flow through said conduit comprising:

first valve means proximal to said fluid-containing reservoir for restricting the flow of fluid through said conduit;

second valve means distal from said reservoir for restricting the flow of fluid through said conduit;

pump means located between said first and second valve means for alternately increasing and decreasing the volume of a portion of said conduit, said first valve means restricting the flow of fluid while said pump means is decreasing said conduit volume and said second valve means restricting the flow of fluid while said pump means is increasing said conduit volume;

first monitoring means for generating a first signal related to the electrical resistance of said fluid between two points located within said conduit and on opposite sides of said first valve means;

second monitoring means for generating a second signal related to the electrical resistance of said fluid between two points located within said conduit and on opposite sides of said conduit portion whose volume is alterable by said pump means; and third monitoring means for generating a third signal related to the electrical resistance of said fluid between two points located on opposite sides of said second valve means, said first, second and third signals being related to the cross-sectional area of said conduit portion containing said first valve means, said conduit portion whose volume is alterable by said pump means, and said conduit portion containing said second valve means, respectively, changes in said cross-sectional areas with respect to each other being related to fluid flow through said conduit.

8. The means useful for measuring of claim 7 wherein said device is an implantable device, said device further comprising an implanted means for telemetering signals related to said first, second and third signals to an externally located receiving means.

9. The means useful for measuring of claim 7 wherein said first monitoring means comprises:

a first pair of electrodes each located at one of said two points; and a flow detector for generating a first voltage related to the electrical resistance between said first pair of electrodes.

10. The means useful for measuring of claim 7 wherein said first monitoring means comprises:

a constant current source;

a first pair of electrodes each located so as to bracket said two points located within said conduit, said first pair of electrodes being connected to said constant current source;

a second pair of electrodes located within said conduit at said two points; and means for measuring the voltage drop between said second pair of electrodes, said voltage drop comprising said first signal.

11. The means useful for measuring of claim 7 wherein said second monitoring means comprises:

a constant current source;

a first pair of electrodes each located so as to bracket said two points located within said conduit, said first pair of electrodes being connected to said constant current source;

a second pair of electrodes located within said conduit at said two points; and means for measuring the voltage drop between said second pair of electrodes, said voltage drop comprising said second signal.

12. The means useful for measuring of claim 7 further comprising a fourth monitoring means for generating a fourth signal related to the electrical resistance between two points located in a portion of said conduit having a constant cross-sectional area, said fourth signal being useful for determining the resistivity of said fluid.

13. The means for measuring of claim 7 wherein said first monitoring means comprises:

a tube having both ends in fluid communication with said conduit, the two ends being on opposite sides of said first valve;

means for inducing a voltage differential across the fluid present in both ends of said tube; and means for measuring current flow through said tube, said current flow being related to the cross-sectional area of said conduit portion located between said tube ends.

14. The means for measuring of claim 7 wherein said second monitoring means comprises:

a tube having both ends in fluid communication with said conduit, the two ends being on opposite sides of said conduit portion whose volume is alterable by said pump means;

means for inducing a voltage differential across the fluid present in both ends of said tube; and means for measuring current flow through said tube, said current flow being related to the cross-sectional area of said conduit portion located between said tube ends.

15. The means for measuring of claim 7 wherein said third monitoring means comprises:

a tube having its two ends in fluid communication with said conduit, the two ends being on opposite sides of said second valve;

means for inducing a voltage differential across the fluid present in the two ends of said tube; and means for measuring current flow through said tube, said current flow being related to the cross-sectional area of said conduit portion located between said tube ends.

16. In a device for dispensing fluid into a user's body, said device having a reservoir means and a conduit in fluid communication with said reservoir means for carrying fluid from said reservoir means to a user's body, a first valve means located proximal to said reservoir means for restricting the flow of fluid through said conduit, a second valve means located distal to said reservoir means for restricting the flow of fluid through said conduit, and a pump means located between said first and second valve means for aternately increasing and decreasing the volume of a portion of said conduit between said first and second valve means, a means useful for measuring fluid flow comprising:

first means for generating a first signal related to the electrical resistance of said fluid within a first predetermined portion of said conduit, said first predetermined portion containing said first valve means;

second means for generating a second signal related to the electrical resistance of said fluid within a second predetermined portion of said conduit, said second predetermined portion containing the portion of said conduit whose volume is alternately increased and decreased by said pump means; and third means for generating a third signal related to the electrical resistance of said fluid within a third predetermined portion of said conduit, said third predetermined portion containing said second valve means, said first, second and third signals being related to the cross-sectional areas of said conduit portion containing said first valve means, said conduit portion whose volume is alternately increased and decreased by said pump means, and said conduit portion containing said second valve means, respectively, changes in said cross-sectional areas with respect to each other being related to fluid flow through said conduit.

17. The means useful for measuring of claim 16 further comprising fourth means for generating a fourth signal related to the electrical resistance of said fluid within a fourth predetermined portion of said conduit having a uniform cross-sectional profile as fluid flows therethrough, said fourth signal being useful in calibrating said first, second and third signals.

18. The means useful for measuring of claim 17 wherein said device is an implantable device, said device further comprising implantable telemetry means for telemetering signals related to said first, second, third and fourth signals to an externally located receiving means.

19. In a device for dispensing fluid into a user's body, said device including a fluid-containing reservoir and a conduit having a proximal end in fluid communication with said reservoir and a distal end through which fluid from said reservoir can flow, a means useful for measuring fluid flow through said conduit comprising:

pumps means for alternately increasing and decreasing the volume of a portion of said conduit;

valve means for restricting the flow of fluid through said conduit, said valve means being operatively connected to said conduit and located between said pump means and said conduit proximal end, said valve means restricting the flow of fluid when said pump means is decreasing said conduit volume;

first monitoring means for generating a first signal related to the electrical resistance of said fluid between two points located within said conduit and on opposite sides of said valve means; and second monitoring means for generating a second signal related to the electrical resistance of said fluid between two points located within said conduit and on opposite sides of said conduit portion whose volume is altered by said pump means, said first and second signals being related to the cross-sectional areas of said conduit portion affected by said pump means and said conduit portion affected by said valve means, respectively, changes in said cross-sectional areas with respect to each other being related to fluid flow through said conduit.

20. In a device for dispensing fluid into a user's body, said device including a fluid-containing reservoir and a conduit having a proximal end in fluid communication with said reservoir and a distal end through which fluid from said reservoir can flow, a means useful for measuring fluid flow through said conduit comprising:

pump means for alternately increasing and decreasing the volume of a portion of said conduit;

valve means for restricting the flow of a fluid through said conduit, said valve means being operatively connected to said conduit and located between said pump means and said conduit distal end, said valve means restricting the flow of fluid when said pump means is increasing said conduit volume;

first monitoring means for generating a first signal related to the electrical resistance of said fluid between two points located within said conduit and on opposite sides of said valve means; and second monitoring means for generating a second signal related to the electrical resistance of said fluid between two points located within said conduit and on opposite sides of said conduit portion whose volume is altered by said pump means, said first and second signals being related to the cross-sectional area of said conduit portion affected said pump means and said conduit portion affected by said valve means, respectively, changes in said cross-sectional areas with respect to each other being related to fluid flow through said conduit.

21. In a device for dispensing fluid into a user's body, said device having a reservoir means and a conduit means in fluid communication with said reservoir means for carrying fluid from said reservoir means to a user's body, a first valve means located proximal to said reservoir means for restricting the flow of fluid through said conduit means, a second valve means located distal to said reservoir for restricting the flow of fluid through said conduit means, and a pump means located between said first and second valve means for alternately increasing and decreasing the volume of a conduit portion between said first and second valve means, a method useful in measuring fluid flow through said conduit means comprising the steps of:

generating a first signal related to the electrical resistance of said fluid within a portion of said conduit containing said first valve means;

generating a second signal related to the electrical resistance of said fluid within a portion of said conduit that includes the volume of said conduit portion affected by said pump means; and generating a third signal related to the resistance of said fluid within a portion of said conduit containing said second valve means, said first, second and third signals being related to the cross-sectional areas of said conduit portion containing said first valve means, said conduit portion whose volume is alternately increased and decreased by said pump means, and said conduit portion containing said second pump means, respectively, changes in said cross-sectional areas with respect to each other being related to fluid flow through said conduit.

22. The method of claim 21 further comprising the step of generating a fourth signal related to the electrical resistance of said fluid within a portion of said conduit having a uniform cross-sectional area as fluid flows therethrough, said fourth signal being useful in determining the resistivity of said fluid.

23. The method of claim 21 wherein said device is an implantable device, said method further comprising the step of telemetering signals related to said first, second, and third signals to a receiving means located externally with respect to said user's body.

24. In a peristaltic pump having a conduit and at least one valve means for restricting fluid flow through said conduit, a method for determining the position of said valve means comprising the step of generating a signal related to the electrical resistance of fluid between two points located within said conduit and on opposite sides of said valve means, said electrical resistance being related to the cross-sectional area of a portion of said conduit whose cross-sectional area is affected by said valve means, said electrical resistance thus being related to the position of said valve means.

* * * * *